US005622529A

United States Patent [19]

Calabrese

[11] Patent Number: 5,622,529
[45] Date of Patent: Apr. 22, 1997

[54] FLAT CERVICAL COLLAR HAVING A UNITARY CHIN SUPPORT

[76] Inventor: Salvatore Calabrese, 2109 Porter St., Philadelphia, Pa. 19145

[21] Appl. No.: 255,360

[22] Filed: Jun. 8, 1994

[51] Int. Cl.⁶ ........................................................ A61F 5/01
[52] U.S. Cl. ...................... 602/18; 128/DIG. 23
[58] Field of Search ................................ 602/6, 7, 17, 18; 128/DIG. 23; D24/191

[56] References Cited

U.S. PATENT DOCUMENTS

| Re. 32,219 | 8/1986 | Garth . | |
|---|---|---|---|
| 2,911,970 | 11/1959 | Bartels | 602/18 |
| 3,343,532 | 9/1967 | Zumaglini | 128/DIG. 23 X |
| 3,622,057 | 11/1971 | Marker . | |
| 3,756,226 | 9/1973 | Calabrese et al. . | |
| 4,205,667 | 6/1980 | Gaylord, Jr. | 602/18 |
| 4,325,363 | 4/1982 | Berkeley . | |
| 4,401,111 | 8/1983 | Blackstone . | |
| 4,413,619 | 11/1983 | Garth . | |
| 4,538,597 | 9/1985 | Lerman | 602/18 |
| 4,702,233 | 10/1987 | Omicioli | 602/18 |
| 4,712,540 | 12/1987 | Tucker et al. . | |
| 4,745,922 | 5/1988 | Taylor | 602/18 X |
| 4,886,052 | 12/1989 | Calabrese . | |
| 4,940,043 | 7/1990 | Burns et al. | 602/18 |
| 4,987,891 | 1/1991 | Gaylord, Jr. et al. . | |
| 5,010,877 | 4/1991 | Druskoczi | 602/18 |
| 5,038,759 | 8/1991 | Morgenstern | 602/18 |
| 5,058,572 | 10/1991 | Schmid et al. | 602/18 |
| 5,060,637 | 10/1991 | Schmid et al. . | |
| 5,083,553 | 1/1992 | Stevenson et al. . | |
| 5,180,361 | 1/1993 | Moore et al. | 602/18 |
| 5,215,517 | 6/1993 | Stevenson et al. . | |
| 5,230,698 | 7/1993 | Garth | 602/18 |

*Primary Examiner*—Richard J. Apley
*Assistant Examiner*—David R. Risley
*Attorney, Agent, or Firm*—Seidel, Gonda, Lavorgna & Monaco, P.C.

[57] ABSTRACT

A lightweight plastic cervical collar includes a one-piece injected molded body, of a flexibility and length sufficient to enable the body to be wrapped around the neck of a wearer. One or more absorbent compressible foam strips are attached to an inner side of the body. A front section of the body defining part of a front collar half includes a generally T-shape integrally molded chin support. Upper edge portions of the body are made flexible by the provision of elongated openings and integral hinges formed by molded grooves extending generally longitudinally in the body. A first fabric-strip fastener is adhered to the front body section near one free end while a second, matably configured flexible fabric-strip is extended from the free end of the rear body section to join the adjoining collar ends together. Where the molded body extends around a tracheal opening, transverse reinforcement ridges are molded in the body to prevent collapse. A resiliently flexible, generally T-shaped joint at the upper center of the front section of the molded body provides firm yet resilient upward support of the wearer's head while preventing forward or lateral movements of the jaw. Slots are provided along the upper and lower edges of the rear body section to assist in wrapping the collar around the wearer's neck. A series of central openings are also provided in the rear collar half for air circulation.

51 Claims, 10 Drawing Sheets

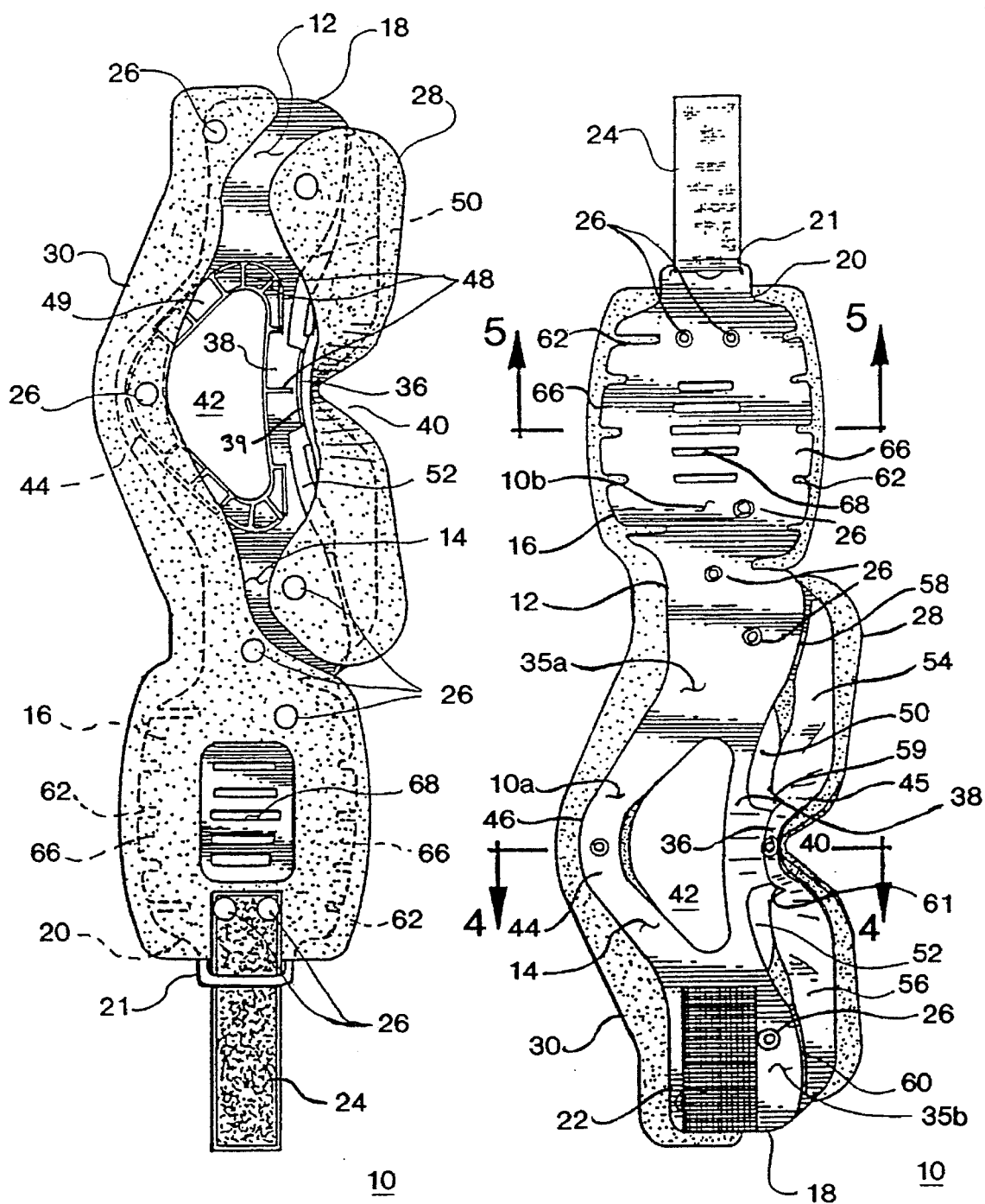

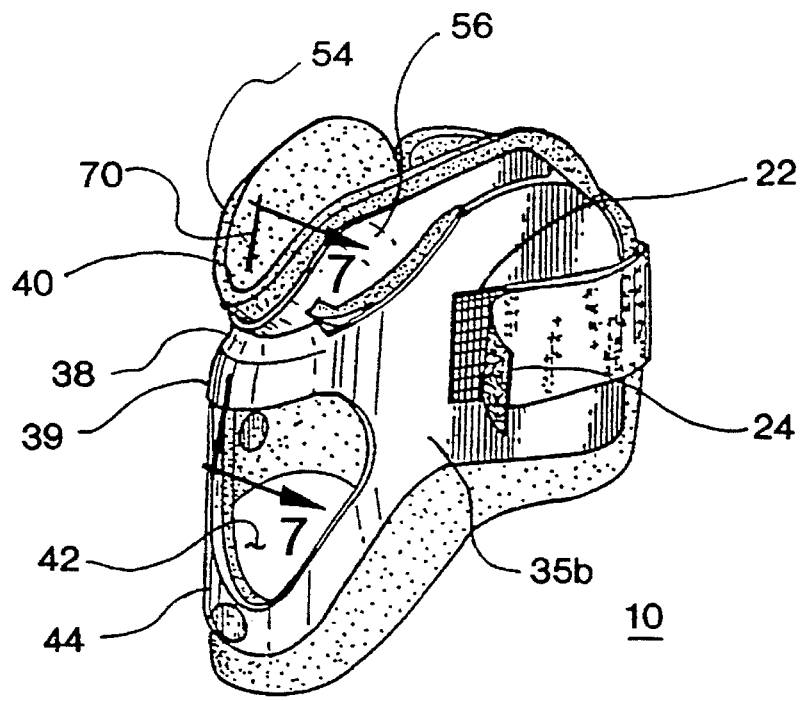
FIG. 6
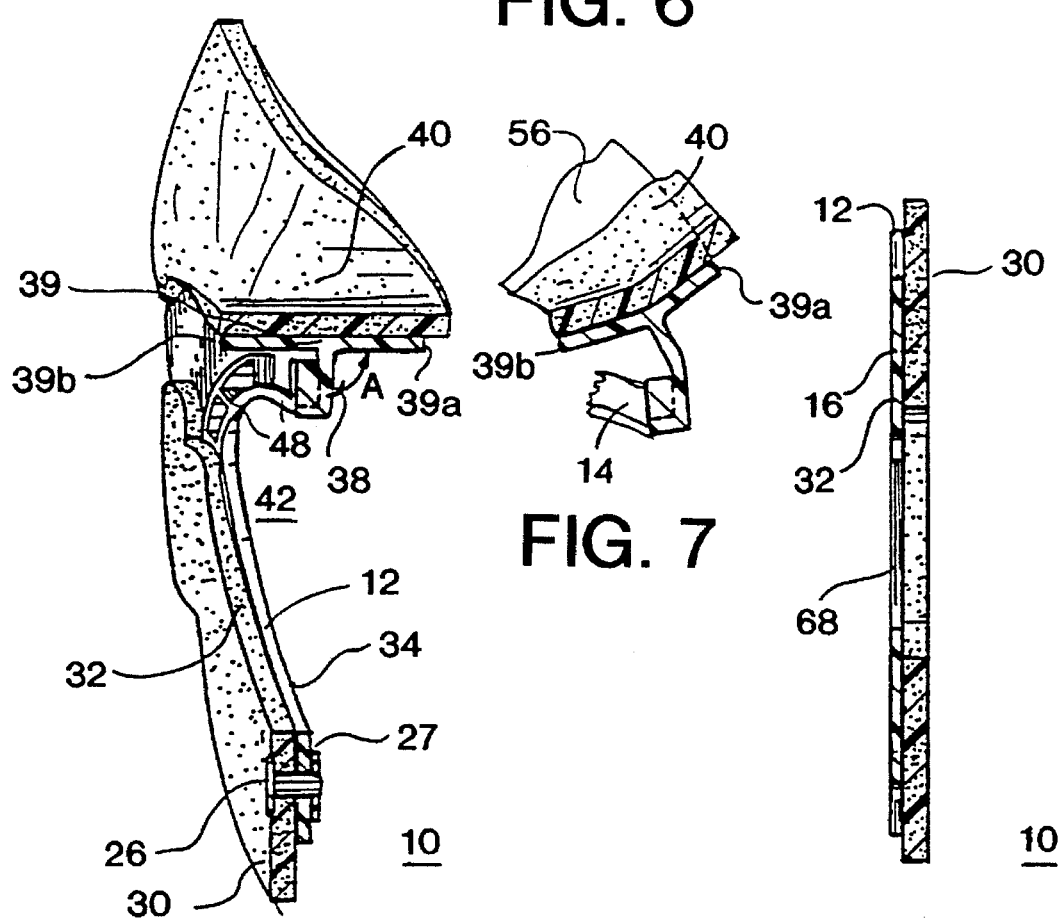
FIG. 7
FIG. 4
FIG. 5

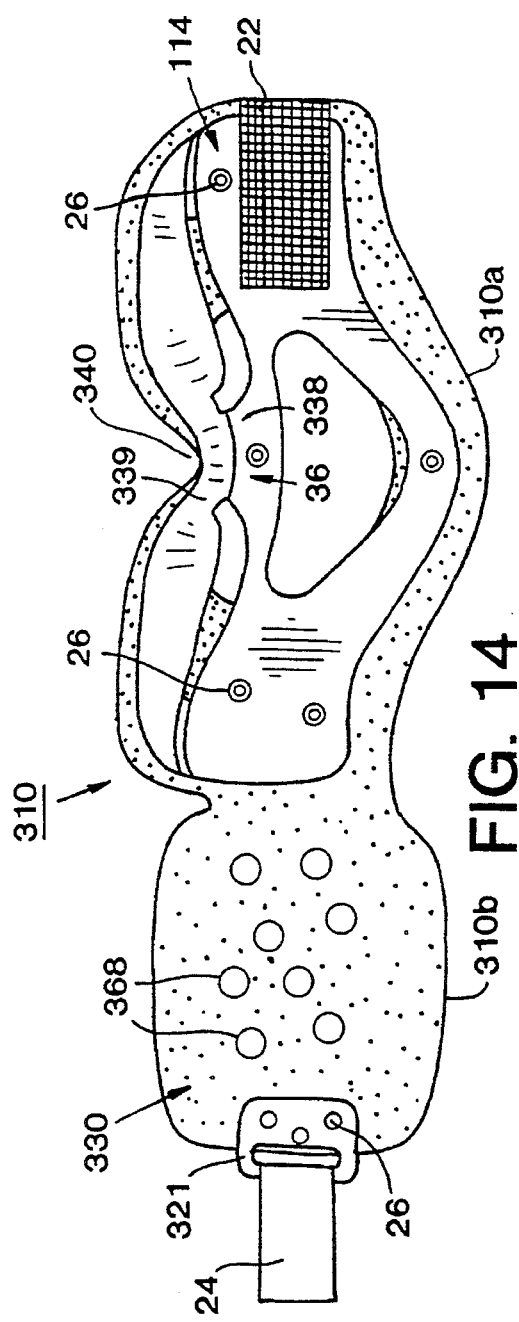
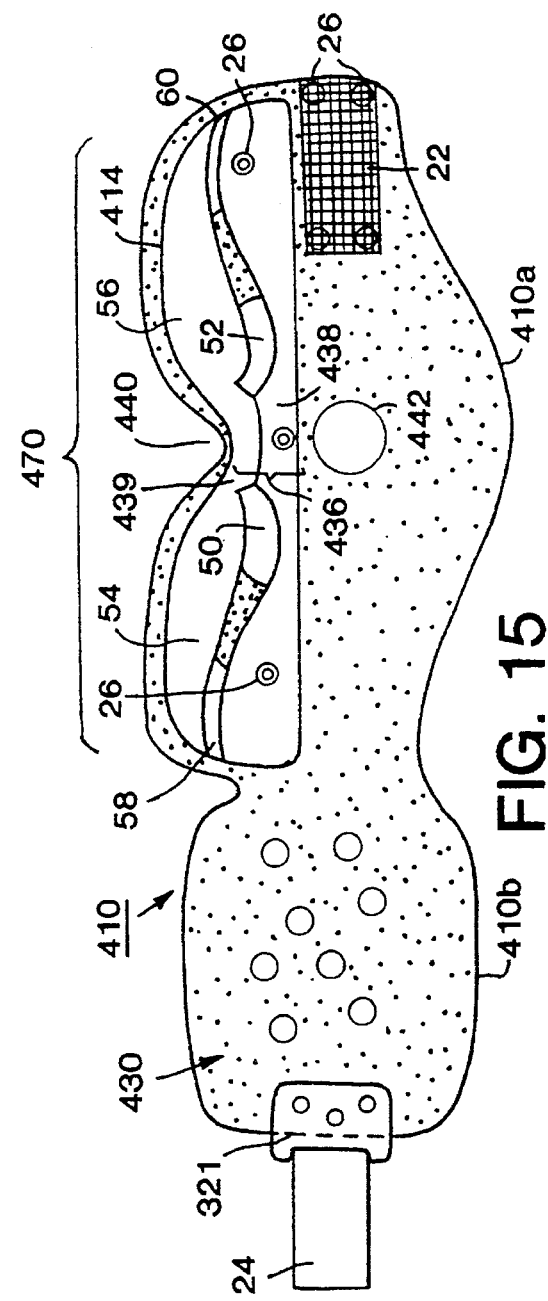

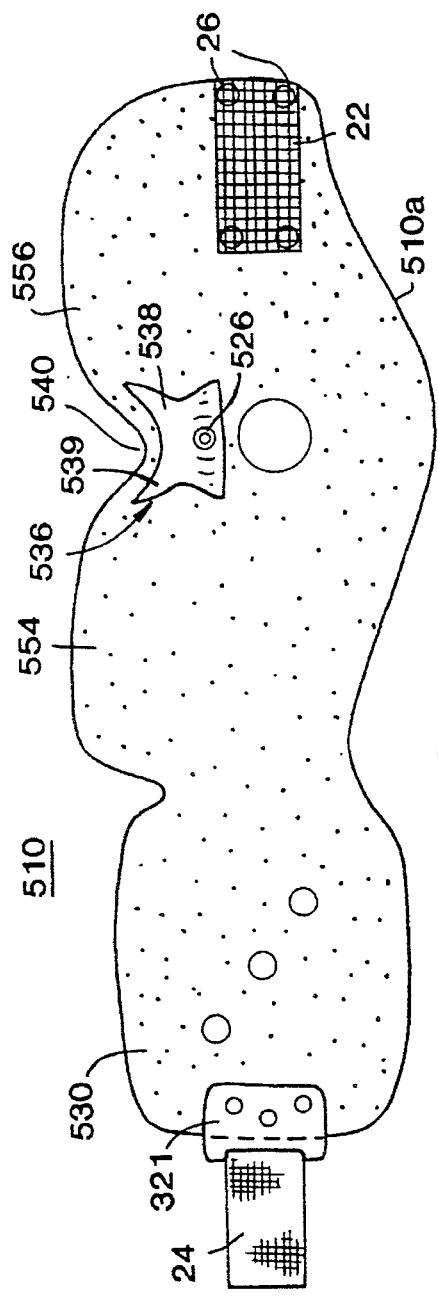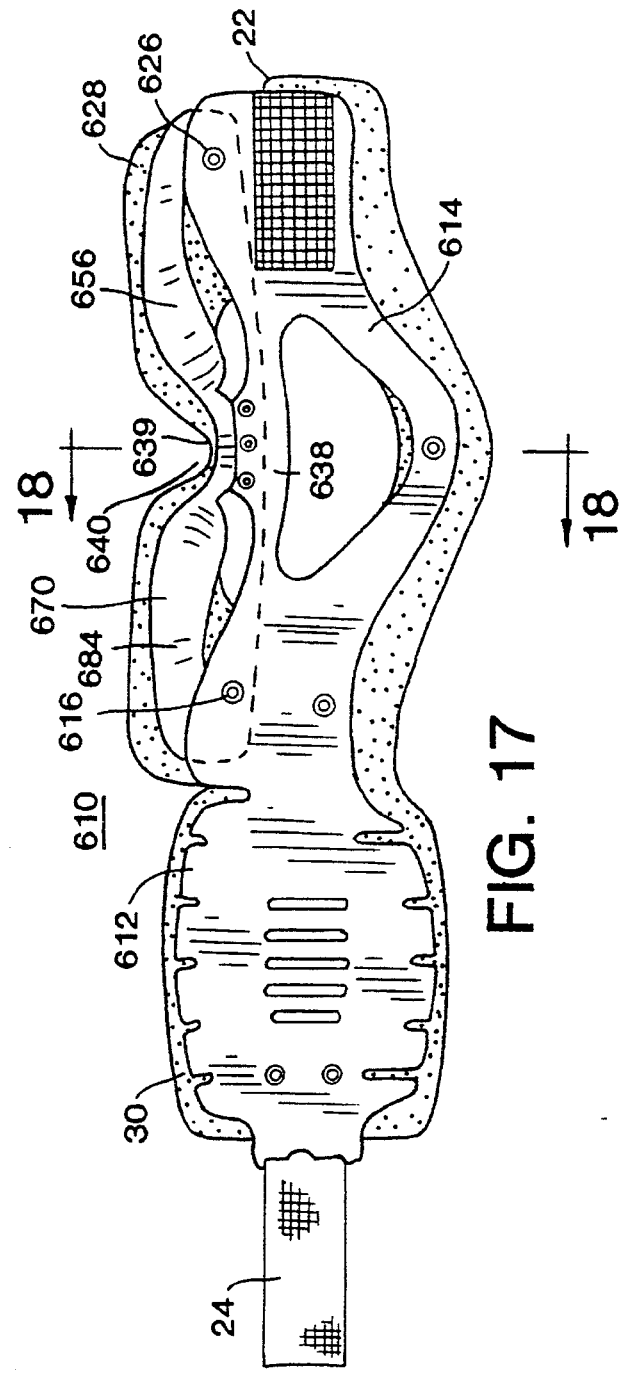

FLAT CERVICAL COLLAR HAVING A UNITARY CHIN SUPPORT

FIELD OF THE INVENTION

The present invention relates to orthopaedic restraints and, in particular, to cervical collars.

BACKGROUND OF THE INVENTION

Lightweight, plastic cervical collars come in a variety of designs. Traditional two-piece collars of the type shown in U.S. Pat. Nos. 3,756,226 and 4,886,052 use semi-circular body halves to provide cervical support. From the method disclosed by U.S. Pat. No. 3,622,057, the body halves are fabricated by shaping pliable cross-linked foam. Despite their acknowledged successful performance, such two-piece collars are considered less desirable than other cervical collars for certain uses. In particular, such collars are considered undesirable for use in emergency vehicles where their relative bulk makes them difficult to store and because of the difficulties that arise from trying to slip a semi-circular rear collar half beneath the neck of an accident victim at the same time the emergency care providers are trying to immobilize the victim.

A number of cervical collars have been designed to respond to this need. These include, for example, those shown in U.S. Pat. Nos. 4,413,619; 4,712,540; 4,987,891; 5,060,637; and 5,215,517. Such collars typically include unitary frontal and rear body sections cut from a non-foamed, relatively stiff, yet flexible plastic sheet. A hybrid cervical collar is shown in U.S. Pat. No. 5,083,553, has also been designed to respond to this need. The disclosed two-piece collar includes separate frontal and rear body sections cut from stiff, flexible plastic sheets.

The above-described collars are typically provided with an integrally attached chin support. This integrally attached chin support is either mechanically fastened to, or monolithically formed with the frontal body section, joining it at the distal ends of the chin support. However, the chin supports on such collars are typically provided as a flat structure, and must be folded into a cup-shape and mechanically fastened at the central portion of the folded frontal body section. This is due to the flat, resiliently flexible plastic sheet construction of the frontal body section and the chin support.

Thus, while certain cervical collars known in the prior art are easy to store and easy to position beneath the neck of an accident victim, it is believed that such collars do not provide the comfort and support provided by traditional two-piece, semi-circular designs.

Moreover, these prior art cervical collars all suffer from a number of drawbacks, especially with respect to the chin support area. Existing collars are fabricated from stiff, flexible plastic sheets requiring that the chin support be mechanically fastened to the frontal body section. This mechanical fastening results in inadequate chin support, lack of stability, and decreased reliability. Due to the fabrication process used for existing collars, there is inadequate support under the chin. This inadequate support causes the head of the wearer to slip from the chin support into the interior of the collar.

Another drawback is that existing fabrication processes typically necessitate a flexible chin support/frontal body section connection. Such connection requires the frontal body section at the chin support area to be bent at an angle to accept the chin support and a fastening. This weakened connection causes increased flexing and decreased rigidity of the chin support and results in an unstabilized cervical-spinal region of the wearer, which can potentially compound the wearer's spinal injuries. Also, during continual use, the mechanical fastenings typically employed to attach chin support to frontal body sections may fail and render the collar useless. Finally, the manufacturing costs associated with providing a mechanical fastening between the chin support and the frontal body section are relatively high due to the manual labor required to accomplish the fastening process.

Therefore, it is believed that there is a long-felt and as yet unsolved need for a substantially flat, one-piece and/or hybrid two-piece collar that can be stored more easily than conventional, semi-circular, two-piece collars but that provides more comfort and more support under the chin than provided by existing designs.

Accordingly, it is an object of the present invention to provide a flat cervical collar, that eliminates the need for a mechanical fastening at the central portion and distal ends of the chin support. It is also an object of the present invention to provide a flat collar that includes a rear or inner chin support ledge which captures the surface area under the region extending from the chin to each ramus of the mandible, thereby limiting flexing relative to the frontal body section and providing added stability to the cervical region.

It is a further object of the present invention to provide a process enabling the frontal body section and the chin support of a collar to be off unitary construction and a contoured three-dimensional configuration.

It is a another object of the present invention to provide a collar with a unitary chin support and a frontal body section construction that minimizes material, manufacturing, and assembly costs.

It is a still further object of the present invention to provide a flat, one-piece or hybrid two-piece, cervical collar fabricated by a process permitting the thickness of components to be independently varied to control the degree of rigidity and flexibility provided by each component.

Yet another object of the current invention is to provide a flat, one-piece or hybrid two-piece, cervical collar that includes mandible supports that can move independently of the frontal body section and each other to more readily adapt to the jaw line of a wearer.

A further object of the present invention is to provide a flat, one-piece or hybrid two-piece, cervical collar with living hinge connections at the distal ends of the mandible support that enable the mandible support to flex and conform to the jaw lines of collar wearers.

Each of the collars of the present invention described below satisfy at least some of these objects and all collars of the present invention collectively satisfy all of these objects.

SUMMARY OF THE INVENTION

It has now been found that these and other objectives are fulfilled by a cervical collar comprising a bendable front collar portion including a frontal body section molded from a substantially incompressible plastic resin and a compressible, flexible foam strip mounted on one side of the frontal body section, where the frontal body section is molded to extend transversely outwardly at the center of the front collar portion from an essentially flat remainder of the front collar portion to define a chin support extending transversely in an upper central portion of the front collar portion. The collar also has an essentially flat, bendable rear collar portion, a fastener strip attached to one of the front collar portion and the rear collar portion proximal a free edge of the one collar portion, and a second fastener strip matingly engageable with the first fastener strip that extends from a free edge of a remaining one of the front collar portion and rear collar portion sufficiently to engage the first fastener strip when the free edge of the front collar portion and the free edge of the rear collar portion are-positioned adjoining one another.

The invention also provides a cervical collar comprising a generally elongated, bendable unitary body molded in one piece from a plastic resin having a frontal body section and a rear body section extending from the frontal body section. The unitary body is of a length and flexibility sufficient to be wrapped into a tubular shape around a wearer's neck with a free edge of the frontal body section preferably adjoining a free edge of the rear body section. The unitary body of the present invention, however, is substantially flat before being wrapped. The unitary body also has a central portion of its frontal body section that is molded to extend transversely from an essentially flat remainder of the body that defines a chin support extending transversely in the upper central portion of the frontal body section. A first fastener strip mounted to the unitary body adjoins one free edge of the body, a second fastener strip, matingly engageable with the first strip, extends from a remaining free edge of the unitary body sufficiently to overlap the first fastener when the unitary body is wrapped into the tubular shape with the free edges at least adjoining one another, and a strip of a compressible flexible foam material mounted on one side of the unitary body forms an inner side of the tubular shape when the unitary body is wrapped into a tubular shape.

In another embodiment of the present invention an improvement in cervical collars including a bendable front collar portion and a normally flat, bendable rear collar portion is provided. The front collar portion includes a frontal body section molded from plastic resin and at least one strip of a compressible flexible foam material mounted to one side of the frontal body section. The collar further includes a first fastener strip attached to one of the front collar portion and the rear collar portion, and a second fastener strip that is matingly engageable with the first strip extends from a free edge of a remaining one of the front and rear collar portions so as to engage with the first fastener strip when the front collar portion and rear collar portion are bent together into a tubular shape around a wearer's neck. In this embodiment the frontal body section is most preferably pre-molded so as to project outwardly on at least one side of the front collar portion opposite the side with the foam strip from between substantially co-planar edge portions of the front collar portion and to define at least a chin support extending transversely in the upper central portion of the front collar portion.

BRIEF DESCRIPTION OF THE DRAWINGS

FIG. 1 is a top plan view of one side of a first embodiment of a cervical collar made in accordance with the present invention;

FIG. 2 is a bottom plan view of the opposite side of the collar of FIG. 1;

FIG. 4 is a cross-sectional view taken along lines 4—4 of FIG. 1;

FIG. 5 is a cross-sectional view taken along lines 5—5 of FIG. 1;

FIG. 6 is a perspective view of the collar of FIGS. 1–5 wrapped into a tubular shape as it would be when worn;

FIG. 7 is a broken away, partial cross-sectional view of the collar of FIGS. 1–6, taken along the lines 7—7 in FIG. 6;

FIG. 14 is a top plan view of another embodiment of a cervical collar of the present invention;

FIG. 15 is a top plan view of another embodiment of a cervical collar of the present invention;

FIG. 16 is a top plan view of another embodiment of a cervical collar of the present invention;

FIG. 17 is a top plan view of another embodiment of a cervical collar of the present invention;

DETAILED DESCRIPTION OF THE PREFERRED EMBODIMENTS

Figure 3:
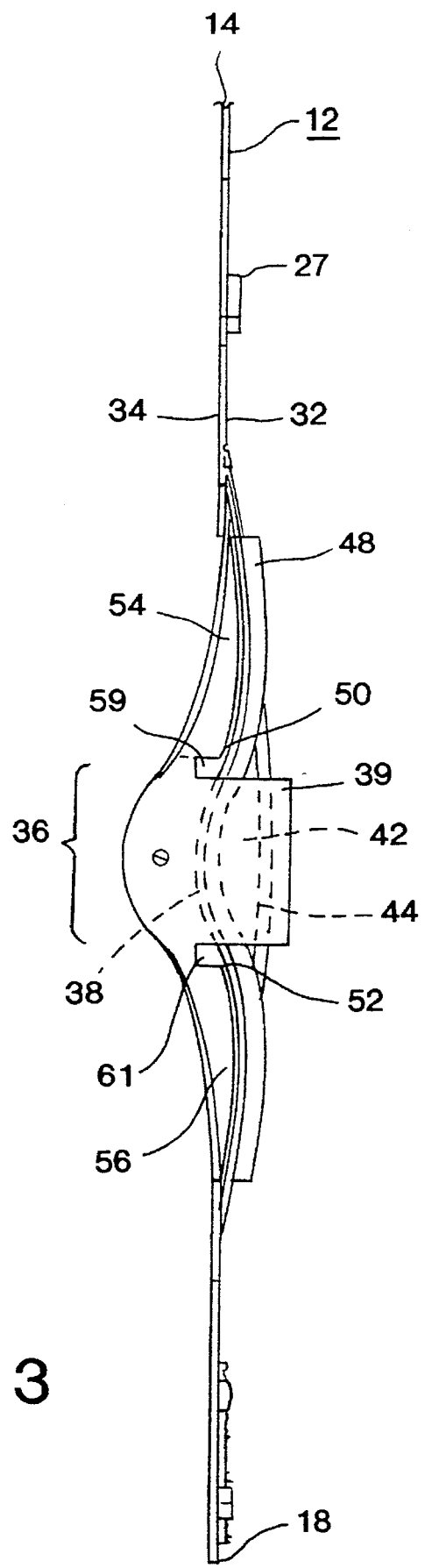
FIG. 3 is a side elevation view of the frontal body section of the collar of FIG. 1.

Referring now to the drawings, in which like reference numerals identify like elements throughout the several views, there is shown in FIG. 1 a one-piece cervical collar 10 of the present invention that includes a bendable front collar portion 10a, that defines a front side of the collar 10 in use, and a bendable back collar portion 10b, that extends unitarily from the front section 10a in this embodiment and defines a back collar portion 10b of the collar 10 when in use. The collar 10 preferably comprises a generally elongated bendable, unitary body 12 preferably fabricated by a molding process, and is most preferably injection molded in one piece from a lightweight, flexibly resilient, substantially incompressible material, such as a suitable thermoplastic resin. This molding process permits the provision of a three-dimensional, contoured shape to the elongated body 12, as described below. The body 12 includes a frontal body section 14 and a rear body section 16, which extends unitarily from one side of the frontal body section 14.

The collar 10 (and the unitary body 12) are of a length and flexibility sufficient to be wrapped into a tubular shape as shown in FIG. 6, with a free edge 18 of the frontal body section 14 at least adjoining a free edge 20 of the rear body section 16 so as to form an at least essentially tubular shape of the unitary body 12. The unitary body 12 should be bendable, and even flexible, but should be sufficiently rigid to provide cervical support when wrapped into the tubular shape shown in FIG. 6. In accordance with one aspect of the present invention the unitary body 12 is preferably molded to be substantially flat prior to use and, with a few exceptions, the unitary body 12 is essentially flat in the configuration shown in FIGS. 1–2 (and in other embodiments) before being wrapped with a tubular shape as shown in FIG. 6.

Other elements of the collar 10 of the present invention include a first fastener strip 22, which is coupled with and preferably fixedly attached by suitable mechanical or chemical means, such as adhesives, rivets, stitching, welding, integral molding, etc., to the unitary body 12 proximal the free edge 18 of the frontal body section 14. The fastener 22 is most preferably a Velcro® hook-type fabric fastening strip. A second fastener 24, that cooperates with the first fastener 22, is also attached at one end to the rear body section 16 of the unitary body 12 by suitable means like those listed above, and most preferably is affixed by rivet fasteners 26. The second fastener 24 is preferably a flexible strip, which is preferably passed through a loop 21 unitarily molded into the extreme free edge 20 of the unitary body 12 and thus extends from the free edge 20 sufficiently to overlap and engage the first fastener (as shown in FIG. 6) when the elongated body 12 is wrapped into a tubular shape. The second fastener 24 is most preferably a fabric strip having a multiplicity of exposed thread loops, which matingly engage with the hook-type fasteners of the preferred first fastener strip 22 described above.

Referring now to FIG. 2, the opposite side of the collar 10 shown in FIG. 1 is illustrated. Compressible flexible foam strips 28, 30 are mounted on to one side 32 of the body 12, which forms an inner side of the collar 10 when wrapped into the tubular shape shown in FIG. 6. The strips 28, 30 may be mounted by any suitable means and are preferably permanently affixed by means including adhesives and/or mechanical fasteners, most preferably thermoplastic rivet fasteners 26, as shown.

As is best seen in FIG. 1, the frontal body section 14 is preferably generally symmetric with respect to a centerline running through section line 4—4. According to one aspect of the invention, a central portion of the frontal body section is molded to extend or project transversely outwardly from between essentially flat side edge or "wing" portions 35a, 35b that form an essentially flat remainder of the frontal body section 14. More preferably, an upper central portion 36 of the frontal body section 14 includes a transversely projecting support member 39, which is unitarily formed with an adjoining medial central portion 38, to define at least part of a transversely extending chin support 40 along the upper central portion 36 of the frontal body section 14.

An enlarged tracheal opening 42 is preferably medially located in the front collar section 10a between the upper central portion 36 and a lowermost central portion 44 of the frontal body section 14. The frontal body section 14 includes an upper edge 45, and a lower edge 46 that is preferably scalloped to conform to the sternum and clavicle area of a patient wearing the collar 10. Due to the central location and preferred enlarged size of the tracheal opening 42, it is desirable to reinforce the center of frontal body section 14 to prevent it from tending to collapse. Preferably reinforcement is provided by means of a plurality of unitarily molded ribs 48, shown in FIG. 2, that extend unitarily and transversely from the main portion of the unitary body 12 proximal to, and preferably immediately adjoining, the tracheal opening 42. Preferably the plurality of ribs 48 define close-sided cells 49, that preferably extend at least along lateral sides of the tracheal opening 42; this structure tends to prevent collapse of the body in a vertical direction (i.e., the axial direction when in the tubular configuration in FIG. 6).

Referring again to FIG. 1, a pair of elongated openings 50, 52 are preferably provided flanking either of two opposing sides of the transversely extending upper central portion 36. The openings 50, 52 define a pair of corresponding lateral upper edge portions 54, 56, respectively, of the frontal body section 14. Preferably, the lateral upper edge portions 54, 56 are each unitary with the transversely extending upper central portion 36. Preferably, notches 59, 61 are provided at the points of intersection between the lateral upper edge portions 54, 56 respectively, and the upper central portion 36. Notches 59, 61 serve to relieve the stress caused by the bending of the lateral upper edge portions 54, 56 as described below and permit the collar to form a shape that better fits the anatomy of each individual patient.

Each of the lateral edge portions 54, 56 extends from the upper central portion 36 toward the rear body section 16 and the free edge 18, respectively. Preferably, a separate unitary hinge connects each distal end of each lateral upper edge portion 54, 56 with a respective remainder of the elongated body 12 at an end of a proximal one of the pair of elongated openings 50, 52 remote from the transversely extending upper central portion 36. Each hinge is preferably defined by a groove 58, 60 preferably formed by a molding process that varies the thickness of the unitary body 12 in the vicinity of the grooves 58, 60. By molding the unitary body 12 with grooves 58, 60, the pair of lateral upper edge portions 54, 56 can be formed so that when in use they twist from an initial orientation, at least partially co-planar with the adjoining wing portions 35a, 35b of the frontal body section, to an orientation extending substantially transverse to the adjoining portion of the frontal body section 14, thereby conforming to each patient's unique jaw line.

As explained above, each of the rear collar portion 10b and rear body section 16 is preferably essentially flat. Rear body section 16 preferably is provided with a number of parallel slots 62, each of which extends transversely into the elongated body 12. The slots 62 are provided extending inwardly from "upper" and "lower" respective edges of the rear body section 16. The slots 62 may be of a uniform length, or certain slots may vary in length, as illustrated. Whether of uniform length or of varying length, the slots 62 define a plurality of fingers 66. The fingers 66 of the longest length are most easily bent, which contributes to the overall flexibility of the rear body section 16 around the wearer's neck and permits the lower edge of the rear body section 16 to more readily conform to the back and shoulder area of the patient wearing the collar 10. In preferred embodiments, a plurality of centrally located openings 68 are also provided to permit air circulation through the rear body portion 16 while the collar 10 is being worn and further enhance the flexibility of this section of the collar 10.

In accordance with one aspect of the present invention, molding the unitary body 12 enables certain selected portions to be three-dimensionally shaped or configured, and also of varied thickness. Preferably, the three-dimensionally contoured parts of elongated body 12 are: (1) the upper central portion 36, (2) the adjoining lateral upper edge portions 54, 56 (to the extent needed to extend those portions from central portion 36 to their opposing distal ends where upper edge portions 54 and 56 are essentially co-planar with the side edge portions 35a, 35b of the body 12 and front collar portion 10a), (3) the plurality of molded ribs 48 reinforcing the body around the tracheal opening 42, and (4) a plurality of rivet bosses 27, that are preferably provided, as seen in FIG. 4, to reinforce the openings through which the stem of each rivet fastener 26 passes. The remainder of the elongated body 12 is preferably essentially flat before being wrapped and is therefore preferably of a uniform thickness.

As best seen in FIG. 4, the reinforcement ribs 48 are preferably substantially equal in thickness and in depth. It will be appreciated that the thickness of the transversely extending upper support member 39 and ribs 48 may be slightly downwardly tapered as they extend away from the main web essentially defining the remainder of the unitary body 12 to assist in separating the elongated body 12 from its mold.

Referring now to FIGS. 1–4, the medial central portion 38 of elongated body 12 in the region above tracheal opening 42 and below the upper support member 39 is preferably molded in an outwardly curved configuration, preferably extending in an arc transversely outwardly beyond the outward extent of lowermost central portion 44 and the remaining side edge portions 35a, 35b (seen in FIGS. 1–2) of the frontal body portion 14. The upper support member 39 is pre-configured into the final shape desired when the elongated body 12 is wrapped into a tubular shape, as shown in FIG. 6, as it would be when applied about the neck of a patient. In other words, the medial central portion 38 is preferably pre-molded into its final shape by being thicker than the remainder of the elongated body 12. It most preferably remains in substantially the same arc independent of the degree to which the unitary body 12 and collar 10 are bent when the collar is applied about the neck of a patient. This increases rigidity of the collar 10, provides enhanced support in the upper central portion 36, and further prevents the tracheal opening 42 from collapsing. The medial central portion 38 of conventional "flat" collars that are bent into their final shape must necessarily be thinner than the "pre-molded" medial central area 38 of collars made in accordance with the present invention which inherently provide greater stability for chin support. Also, the degree of chin support provided by the prior art "bendable" lower central areas depends on the degree of bend of the collar body 12 because the degree of bend of the medial central portion 38 affects the angle of the chin support.

As is further seen in FIGS. 3–4 and the broken away cross-section of FIG. 7, the upper support member 39 preferably includes an outer chin support member portion 39a and an inner chin support member portion 39b, which are unitary. Outer chin support member portion 39a extends beyond the outer extent of medial central portion 38 and inner chin support member portion 39b projects within the outward extent of medial central portion 38. As is best seen in cross-section in FIG. 4, a generally T-shaped joint is formed between transversely extending chin support member 39 and the underlying medial portion 38 of the body. Also, outer chin support portion 39a extends slightly upwardly as it projects transversely outwardly from the outer side 34 of the elongated body 12 while inner chin support portion 39b extends slightly downwardly as it projects from the inner side 32 of the elongated body 12. The lateral upper edge portions 54, 56 extend unitarily away from the outer chin support portion 39a forward of the adjoining medial portion 38 and the remainder of the elongated body 12. Together, as shown in FIG. 6, upper central portion 36 and the lateral upper edge portions 54, 56 define a partially cup-shaped mandible support 70. The upper central portion 36 itself defines a chin support 40 that substantially prevents a forward or downward movement of the wearer's chin, while the lateral upper edge portions 54, 56 define the remainder of mandible support 70 and simultaneously (but independently) prevent lateral mandible movement.

As best seen in FIGS. 4 and 7, which are cross-sectional views of the upper central portion 36 before and after wrapping, respectively, the partial cup-shape of the chin support 40 is deepened and extended as the collar 10 is wrapped to transform it from its initial substantially flat configuration shown in FIGS. 1–5 to the tubular configuration shown in FIGS. 6–7. The chin support member 39a, 39b pitches more steeply when the frontal body section 14 is bent, and unitary hinges formed by grooves 58, 60 further permit the lateral upper edge portions 54, 56 to deflect outwardly a degree sufficient to accommodate the unique jaw line of a particular patient wearing the collar 10. Preferably, the outermost portions of the frontal section 14 along the upper edge 45 are scalloped upwardly so as to cover the temporamandible joint area of the collar wearer, and to assist in immobilizing the jaw as well as the cervical region.

The present invention also discloses fabrication of a flat collar by molding, preferably by injection molding, to permit the formation of a very strong, relatively rigid, three-dimensional thermoplastic chin support and also permit a very strong, yet flexible mandible support capable of contouring to the unique jaw line of a particular patient. Molding of at least the frontal body portion 14 permits both the outer projection of outer chin support portion 39a from the medial central portion 38 and also the co-planar inward projection of inner chin support portion 39b from medial central portion 38 to be formed. It is believed this configuration provides a stiffer and more stable yet comfortable chin and mandible support and restraint than is provided by the more flexible structure of the prior art cervical collars described above. An additional advantage of the collar 10 of the present invention is that it takes up considerably less room than conventional collars. Without packaging or with proper packaging, collars 10 made in accordance with the present invention may be nested so that the projecting upper central portions 36 and the transverse projections 39a, 39b nest, thereby presenting a minimum of storage difficulties.

The ability to transversely extend the upper central portion 36 from the remainder of body 12 greatly affects the ability to control immobilization of the wearer's head. The greater transverse extent, in combination with the upward pitch of member 39, permits the provision of good chin fit with substantial frontal support. Preferably, the front projecting portion 39a of the upper central portion 36 is pivoted at an angle A, seen in FIG. 4, preferably of about a 110° with respect to the adjoining medial portion 38 and the remainder of the unitary body 12.

Unitary body 12 is therefore preferably injected molded from a bendable, substantially incompressible (i.e. non-foamed) thermoplastic resin such as polyethylene. The flexible foam strips 28, 30 are preferably a hydrophobic foam, such as polypropylene or polyurethane, which prevents the absorption of bodily fluids, allowing the collar to be more readily disinfected and reused. Alternatively, the use of hydrophilic foam plastic materials such as polyesters, which absorb bodily fluids from the wearer, allow improved comfort. The use of either type of foam plastic strips lessens the transmittal of pressure of the elongated body 12 on the wearer's face. Although not shown, breathable natural fabric covers can be provided on the inner side of the collar 10 by being permanently affixed over the foam 28, 30 to the body 12 or removably mounted on the collar 10. The foam strips 28, 30 may be cut from a flat plastic sheet material. Preferably, upper and lower edge margins of the foam strips 28, 30 are extended beyond the upper and lower edge margins of the unitary body 12 to present a foam material edge to the wearer's surface for improved comfort. Two foam strips are preferred to one continuous strip since they provide the best possible fit on the body 12. In particular, the upper strip 28 which defines the lining of the mandible support 70 better conforms to this surface when it is independent. The medial upper central portion 36 is preferably pierced to receive a flat-headed rivet that secures the upper foam strip 28 to the upper central portion 36.

Figure 8B:
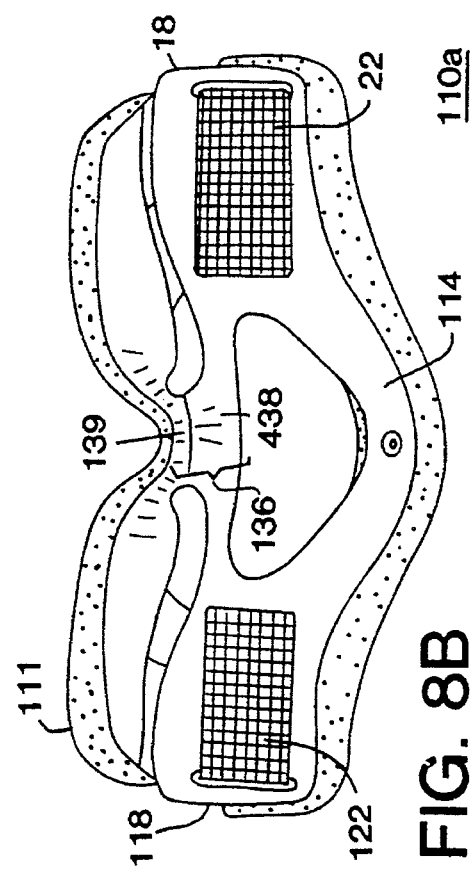
FIG. 8 is a top plan view of a two piece embodiment of the cervical collar of the present invention.
Figure 9B:
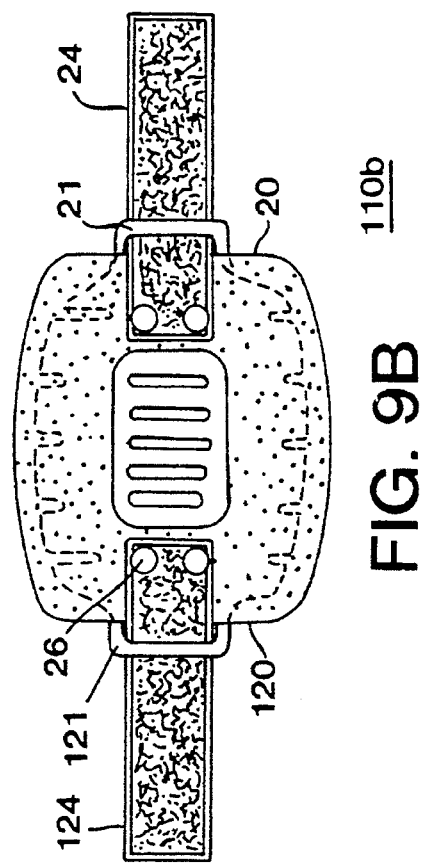
FIG. 9. is a bottom plan view of the two piece collar of FIG. 8.
Figure 8A:
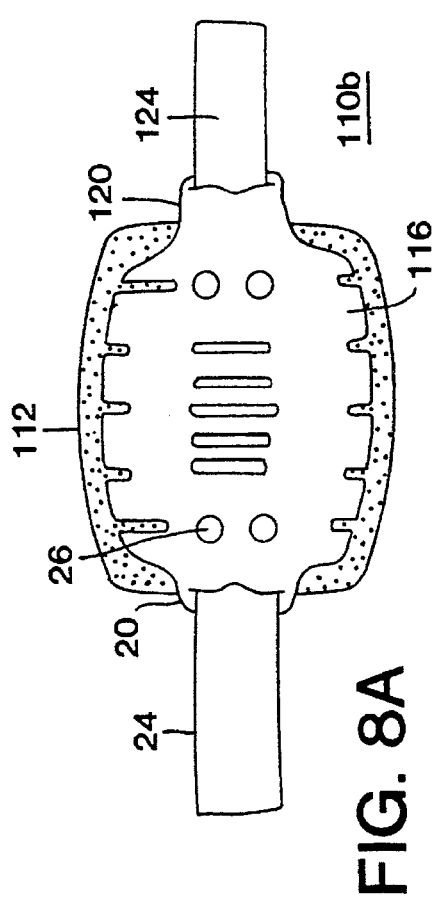
Figure 9A:
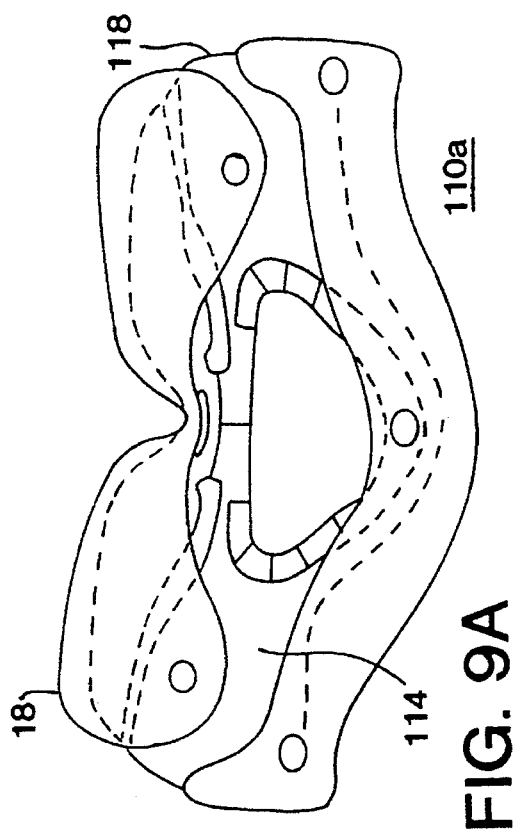
Figure 10:
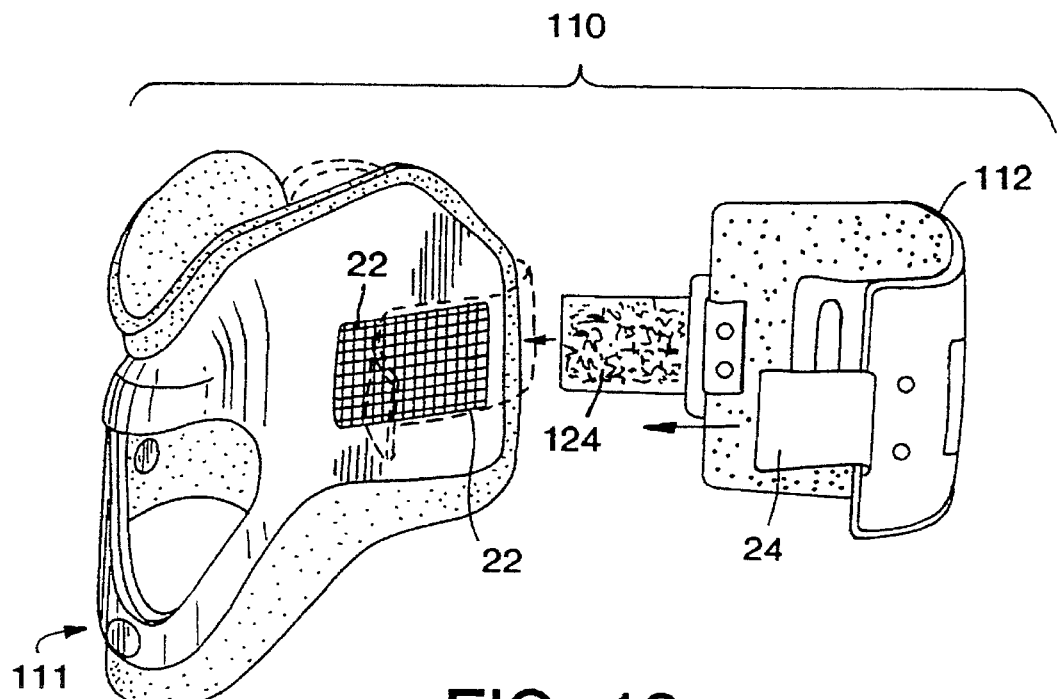
FIG. 10 is a perspective view of the collar of FIGS. 8–9 being joined together into a tubular shape as it would be when worn.

FIGS. 8–10 illustrate a second embodiment of cervical collar that is also constructed in accordance with the present invention, and classified as a "hybrid two-piece" collar, generally designated by the reference numeral 110. As seen in FIGS. 8B and 9A the collar 110 is formed by a substantially flat front collar half 110a and an essentially flat rear collar half 110b seen in FIGS. 8A and 9B. Front collar half 110a includes a frontal body section 114, preferably molded from an essentially incompressible thermoplastic material. Rear collar half 110b includes a rear body section, indicated generally at 116, separate from the frontal body section 114 and preferably similarly molded from the same or a similar material.

Referring now also to FIG. 10, it is seen that the two halves 110a, 110b form the front and rear sides of the collar 110 when the halves 110a, 110b and the body sections 114, 116 are wrapped around a patient's neck. When wrapped, a first free edge 18 of the frontal body section 114 at least adjoins a first free edge 20 of the rear body section 116, while a second free edge 118 of the frontal body section 114 at least adjoins a second free edge 120 of the rear body section 116 so as to form the at least essentially tubular shape of the collar 110, seen in FIG. 10.

Other elements of the collar 110 include first fastener 22 and a second fastener 122, both preferably Velcro® hook-type fastening members which are mounted to and preferably fixedly attached by suitable mechanical or chemical means, preferably adhesive, proximal to the free edge 18 and the free edge 118, respectively, of the frontal body section 114. A third fastener 24 and a fourth fastener 124, preferably Velcro® loop-type fastening members, which matingly engage with the hook-type fasteners preferably used in the first and second fabric fastener strips 22, 122, are mounted to and preferably fixedly attached by suitable mechanical or chemical means, proximal of the free edges 20, 120, respectively, of the rear body section 116. Third fastener 24 and fourth fastener 124 pass through loops 21, 121, respectively, that are unitarily molded into the extreme free edges 20, 120, respectively, of the rear body portion 116. Third fastener 24 and fourth fastener 124 extend from free edges 20, 120, respectively, sufficiently to overlap the first fastener 22 and second fastener 122 respectively, as shown in FIG. 10 when frontal and rear body sections 114, 116 of the collar 110 are wrapped into the tubular shape with the free edges 18, 20 and free edges 118, 120 at least adjoining or overlapping one another.

Apart from the provision of the additional releasable fasteners 122, 124, loop 121 and the division of the unitary body 12 of collar 10 into two parts 114 and 116, collar 110 is otherwise substantially identical to collar 10 described above with reference to FIGS. 1–7.

Figure 12:
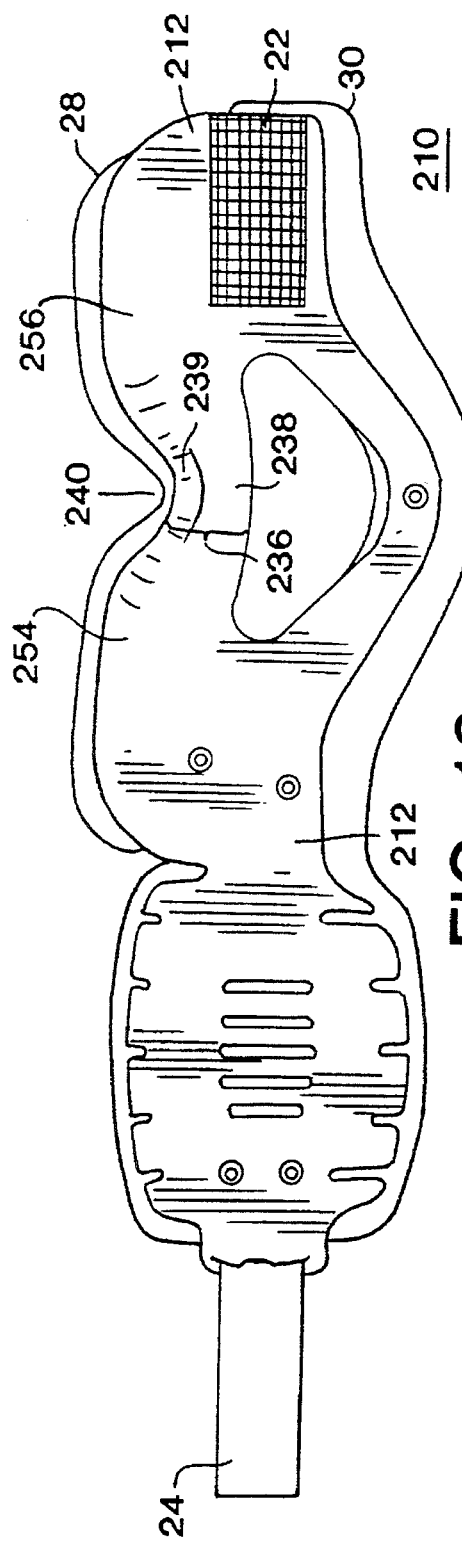
FIG. 12 is a top plan view of an embodiment of a cervical collar of the present invention without mandible support openings.
Figure 13:
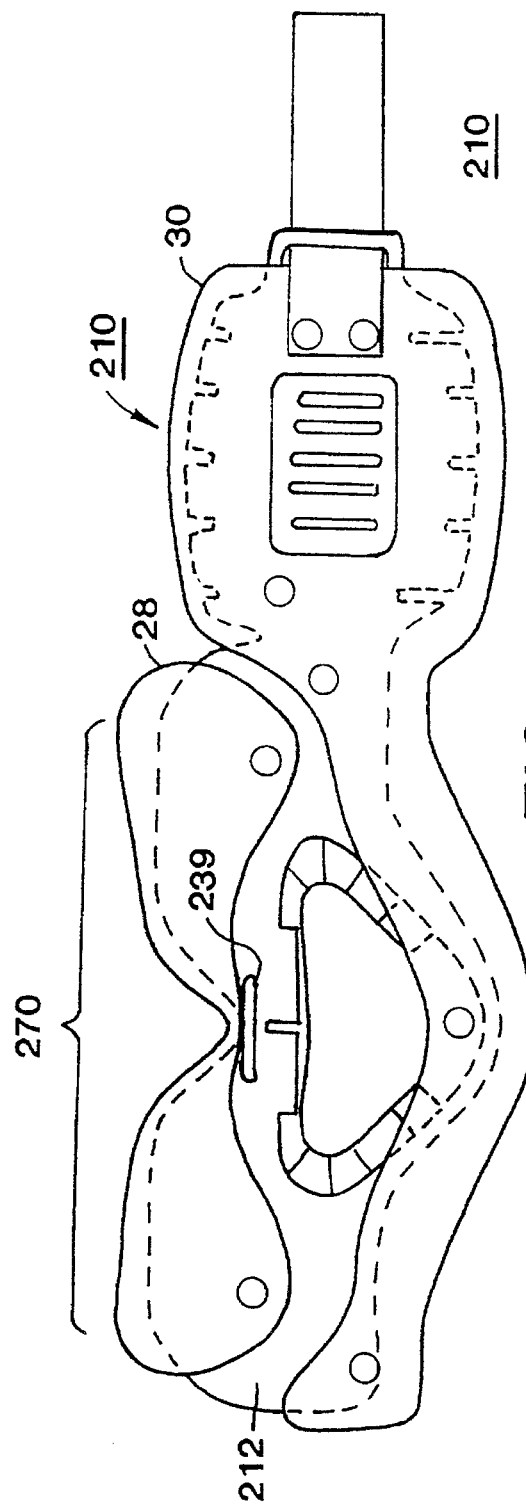
FIG. 13 is a bottom plan view of the collar of FIG. 12.

FIGS. 12–13 illustrate a third embodiment of a one-piece, flat cervical collar constructed in accordance with the present invention and generally designated by the reference numeral 210. The cervical collar 210 of this embodiment is substantially similar to the collar 10 described above, and like reference numerals reference similar elements. In the embodiment illustrated in FIG. 12, the elongated openings 50, 52, grooves 58, 60, and notches 59, 61 seen in FIGS. 1–7 are omitted. As a result, lateral upper edges 254 and 256 are now unitarily molded with the remainder of an elongated body 212 and provide increased lateral support for the mandible when the collar 210 is wrapped around the neck, as shown in FIG. 1. As seen in FIGS. 12–13 the chin support 240 and the overall mandible support 270 formed along the upper side of frontal collar portion 210a are also mated with protruding upper central portion 236. It should also be understood, however, that collar 210 may be fabricated as a hybrid two-piece collar in accordance with transformation of the design of the first embodiment illustrated in FIGS. 1–7 into the second embodiment illustrated in FIGS. 8–10.

Figure 11:
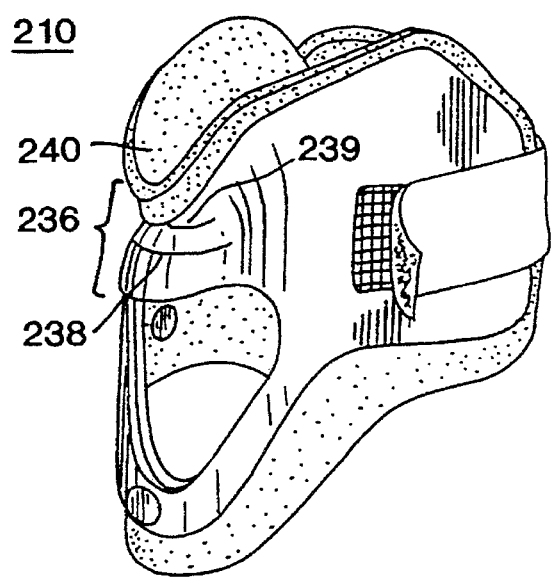
FIG. 11 is a perspective view of the collar of FIGS. 9–10 wrapped into a tubular shape as it would be when worn.

FIGS. 14–21 illustrate additional embodiments of cervical collars constructed in accordance with the present invention. Among other things, these embodiments illustrate various ways in which the present invention can be incorporated or retrofitted into existing cervical collars. FIGS. 14–16, for example, depict flat, one-piece cervical collar embodiments according to the present invention indicated generally at 310, 410, 510, respectively, in which progressively smaller unitary molded bodies are provided. In the collar 310 shown in FIG. 14, the frontal collar section 310a includes a frontal body portion 314, substantially identical to frontal body portion 114 of the collar 110, illustrated in FIGS. 11–13, except for the deletion of fastener strip 122. A second fastener strip 24 is attached instead directly to a compressible, flexible foam strip 330 forming the entirety of the rear collar portion 310b and extending unitarily on to the inner side of frontal body portion 114 and attached by suitable means such as the rivet fasteners 26 described above. A pair of identical looped members 321 are preferably applied to either side of foam 330 to spread the attachment loads over a broader area. Air holes 368 substitute for the slots 68 shown in FIGS. 1–2 to maintain ventilation in the rear collar half 310b.

FIG. 15, illustrates an embodiment of a cervical collar 410 that includes a substantially one-piece compressible, flexible foam body 430 defining a front collar portion 410a and a unitary rear collar portion 410b. Preferably, a molded plastic shortened support body 414 is mounted and secured to an upper portion of the front body section 414 by suitable means, and defines a mandible support 470, that includes an upper central portion 436, which protrudes outwardly from a remainder of the collar 410 and which includes along its central upper edge a protruding medial central portion supporting a transversely extending member 439 defining at least part of a chin support 440 of an overall mandible support 470. Elongated openings 50, 52 define, in part, lateral upper edge portions 54, 56, respectively. Such portions as well as living hinges are further defined by grooves 58, 60 as described above. Due to the decrease in vertical support as a result of the limited extent of the mandible support 470, a tracheal opening 442, smaller than the opening 42 shown in FIGS. 1–2, is most preferably provided. Also, fastener strip 22 is again secured directly to foam strip 430, preferably by rivet fasteners 26 as described with reference to FIG. 14.

FIG. 16 depicts a one-piece, flat collar made in accordance with the present invention indicated generally at 510, in which the collar is almost entirely provided by a unitary, flexible, compressible foam body 530 and which is minimally reinforced with a frontal body portion 536 in an upper central area of the front half 510a of the collar. The frontal body portion 536 includes a transversely extending upper support member 539 supported by a generally partial cup-shape medial central portion 538, which is itself mounted by suitable means such as a rivet fastener 526 to the foam body 530 thereby defining a chin support 540. Mandible support is provided by unitary upper edge portions 554, 556 of the foam body 530. Otherwise, the indicated changes are similar to those incorporated into the embodiments of FIGS. 14–15.

Another cervical collar 610 is illustrated in FIG. 17, and differs from the prior embodiments of FIGS. 1–16 in that a separate mandible support member 670 is attached to a separate molded unitary body 612 by suitable means such as rivet fasteners 626. The unitary body 612 is again, however, essentially flat. An upper, centrally located portion 638 of a frontal section 614 of the unitary body 612, which is initially essentially flat and co-planar with the remainder of body 612 and collar 610, is coupled with and preferably fixedly attached to a chin support portion 639 of the mandible support 670 through a laterally curved base 639c. The base 639c is preferably molded unitarily with and supports outwardly and inwardly transversely extending chin support projections 639a, 639b. Lateral portions 654, 656 unitarily formed with and extending away from the projecting chin support projections 639a, 639b and foam strip 628 define the remainder of the flexible mandible support 670.

Figure 18:
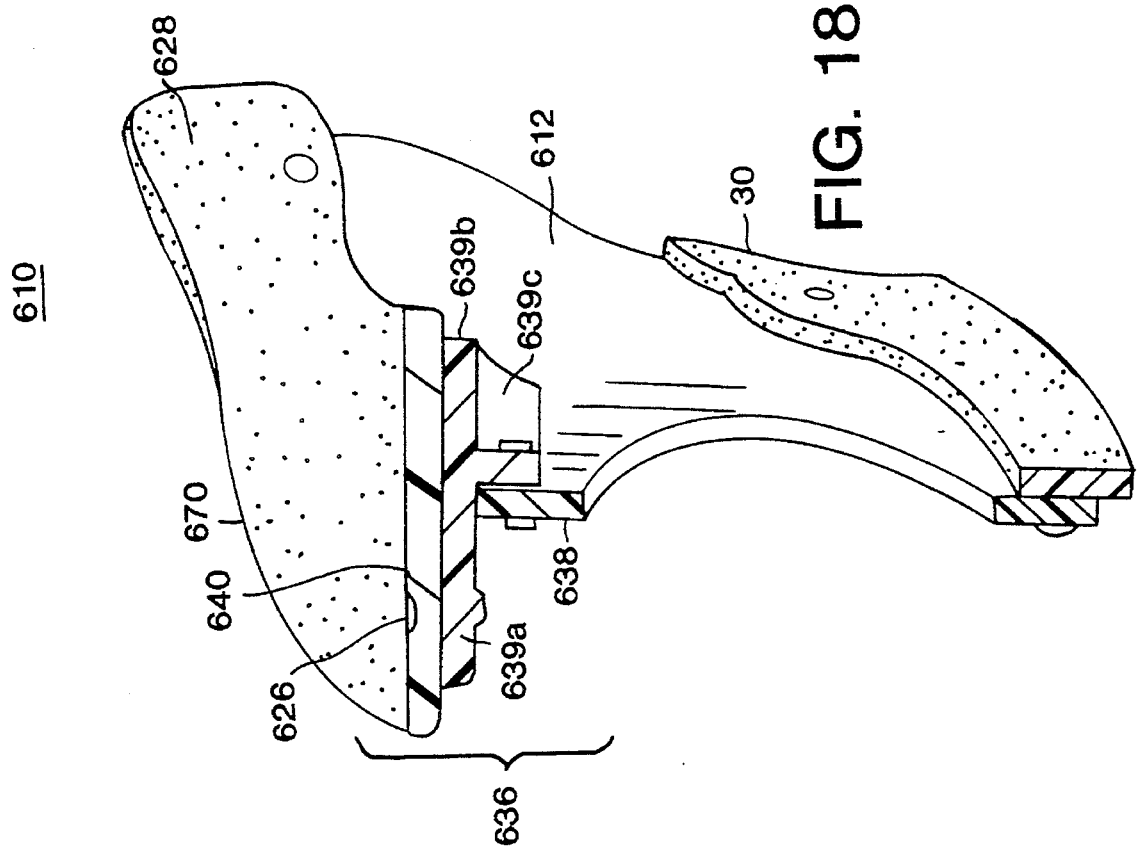
FIG. 18 is a broken away, cross-sectional view of the cervical collar of the present invention, taken along the lines 18—18 of FIG. 17, illustrating the addition of a transverse chin support member.

FIG. 18 depicts the manner in which the transversely extending projections 639a, 639b are preferably secured to the upper centrally located portion 638 of the unitary body 612 to define (with compressible foam strip 628), a chin rest portion 640 of an overall mandible support 670.

Figure 19:
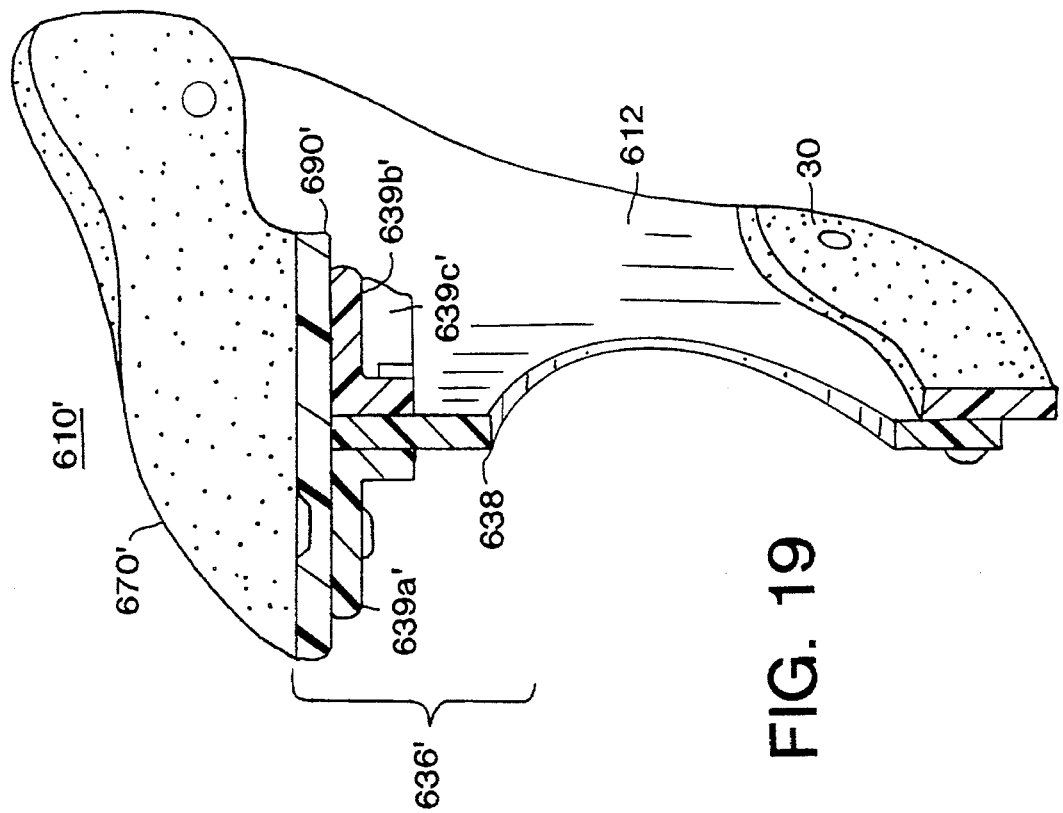
FIG. 19 is a broken away, cross-sectional view of the flat cervical collar of the present invention, similar to FIG. 18, illustrating an alternate embodiment transverse chin support member.

FIG. 19 shows an alternative embodiment of the cervical collar 610 shown in FIGS. 17–18 that is indicated generally at 610'. In this embodiment a molded mandible support member 670' includes only a forwardly extending central transverse projection 639a', which is attached to an outer side of upper central member 638, while a separate, inwardly extending transverse chin support projection 639b' is attached to the opposing, inner side of the upper central portion 638 of the unitary body 612. The downwardly extending bases or legs of transverse projections 639a, 639b are preferably outwardly curved.

Figure 20:
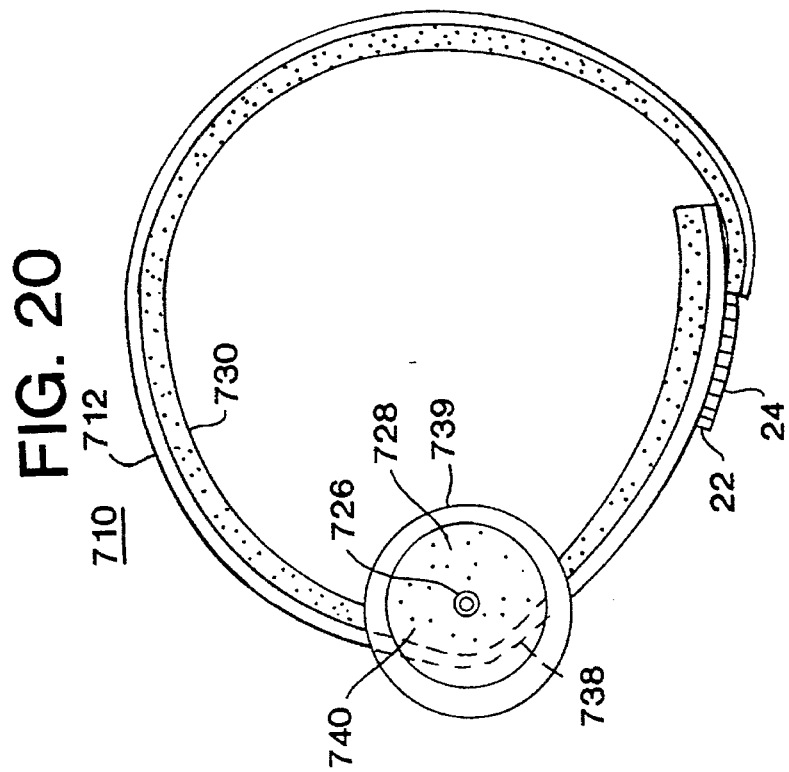
FIG. 20 is a plan view of the collar of FIG. 17 after being wrapped into a tubular form.

In addition to providing full mandible support, it will be appreciated that a simple transverse chin support member similar to portions 639a–639c or portions 639a', 639b' can be mounted to the upper central portion of the front portion of an otherwise conventional cervical collar that lacks lateral portions that form a transversely extending chin support 740, as seen in FIG. 20. In this embodiment, an otherwise flat cervical collar 710, which includes a molded unitary body 712 mounted to a compressible foam strip 730 on its inner side, can now include a chin support 740 that preferably extends both forwardly and rearwardly from the underlying supporting portion 736.

Figure 21:
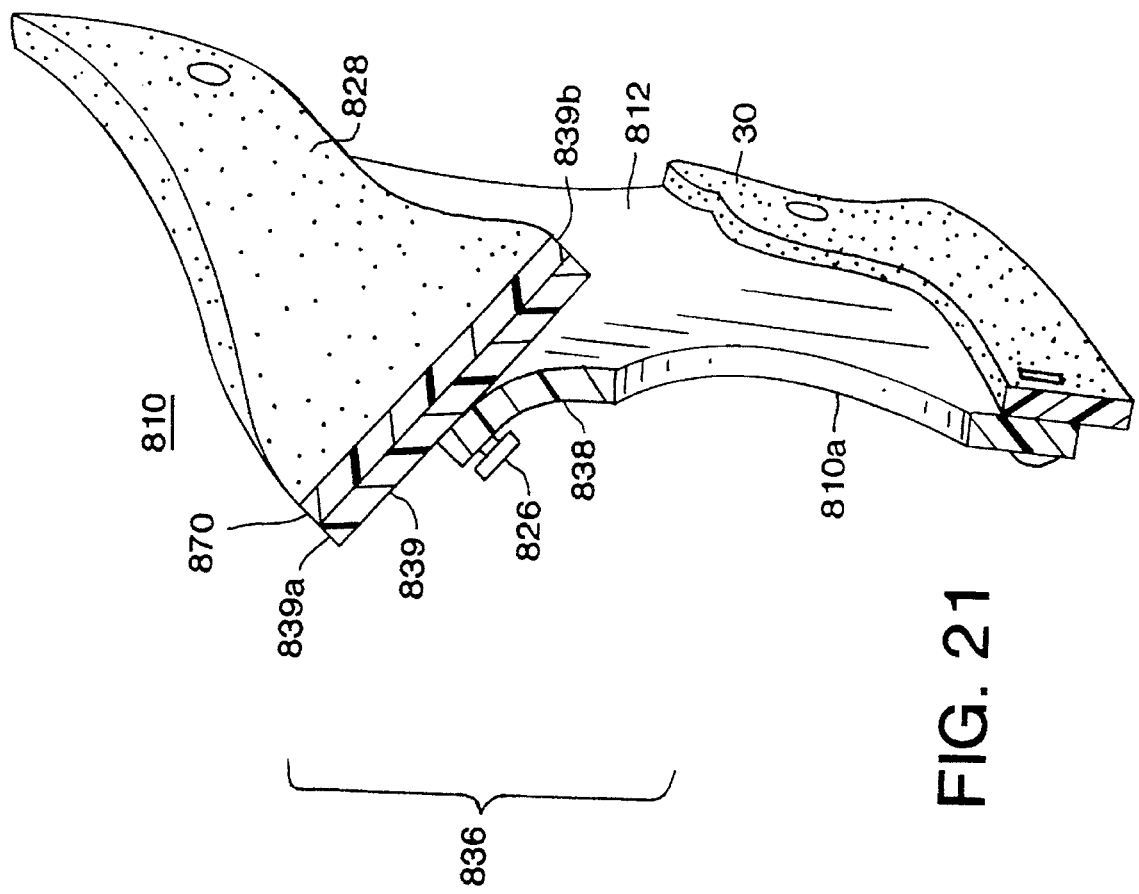
FIG. 21 is a broken away, localized cross-sectional view of a cervical collar illustrating another alternate embodiment of a transversely extending chin support member.

FIG. 21 depicts yet another cervical collar embodiment 810 showing an alternate method of mounting a mandible support member 870. The mandible support 870 has a central, curved transverse chin support portion 839 defining transversely extending chin support projections 839a, 839b and is affixed using a rivet 826 or other suitable attachment to connect the chin support 839 to a flexible upper central portion 838 of a molded unitary body 812, as might be provided in a conventional flat one-piece or hybrid two-piece collar. The resulting structure defines a projecting upper central portion 836 on front collar portion 810a of the collar 810. Since conventional flat one-piece and hybrid two-piece collars generally provide inadequate chin support due to their inherent design limitations as described in detail above, the addition of a premolded, curved, transverse chin support portion 839, including inner chin support projection 839b, would provide additionally needed stiffness and support under the chin of a wearer.

Finally, it should also be understood that any of the previously described one-piece collars may be fabricated as a "hybrid two-piece" collar as explained above with reference to FIGS. 12–13.

While certain preferred embodiments and various modifications thereto have been described or suggested, other changes in these preferred embodiments will occur to those of ordinary skill in the art which do not depart from the broad inventive concepts of the present invention. Accordingly, reference should be made to the appended claims rather than the specific embodiment of the foregoing specification to ascertain the full scope of the present invention.

What is claimed is:

1. A cervical collar comprising:
   (a) a front collar portion having a frontal body section fabricated from a substantially incompressible plastic material and having a unitary chin support extending transversely outwardly from an essentially flat front collar portion,
   wherein the chin support extends transversely in at least an upper central portion of the front collar portion;
   (b) a rear collar portion;
   (c) a compressible, flexible foam strip mounted on one side of at least the frontal body section,
   (d) a first fastener strip attached to one of the front collar portion and the rear collar portion; and
   (e) a second fastener strip extending from a free edge of a remaining one of the front collar portion and rear portion, the second fastener strip engaging the first fastener strip when the collar is placed around a patient's neck.

2. The cervical collar of claim 1 further comprising a mandible support extending from the chin support to a point proximal a free edge of the frontal body section and an opposing end of the frontal body section, wherein the mandible support is sufficiently flexible to conform to the patient wearing the collar.

3. The collar of claim 1 wherein the frontal body section further includes a pair of elongated openings flanking opposing sides of the unitary chin support to define a pair of lateral upper edge portions integral with the upper central portion, each lateral upper edge portion coupled with a remainder of the body at an end of a proximal one of the pair of elongated openings remote from the transversely extending upper central portion through a hinge.

4. The collar of claim 1 wherein the transversely extending upper central portion includes a generally T-shaped joint.

5. The collar of claim 1 wherein the frontal section includes a tracheal opening beneath the transversely extending central portion and adjoining lowermost central portion of the frontal section.

6. The collar of claim 5 wherein the body includes a plurality of reinforcement ribs extending integrally and transversely from the frontal section proximal to the tracheal opening, reinforcing the tracheal opening.

7. The collar of claim 6 wherein the central portion and the reinforcement ridges are of a thickness less than the transverse extent of the central portion and the reinforcement ribs and are substantially equal in thickness to a thickness of at least a substantial remainder of the body.

8. The collar of claim 1 wherein the central portion has a thickness less than the transverse extent of the central portion and is substantially equal in thickness to a thickness of at least a substantial remainder of the body.

9. The collar of claim 1 wherein a central portion of the rear section includes a plurality of air circulation openings extending transversely through the body.

10. A cervical collar comprising:

a bendable one-piece body fabricated from a plastic material, the body comprising a front section and a rear section extending from the front section, the body having a length and flexibility such that the body can be formed into a tubular shape around a patient's neck with a free edge of the front section adjoining a free edge of the rear section, the body having a substantially flat shape before being formed into the tubular shape, said body further comprising an upper central portion of the front section of the substantially flat body extending transversely from a substantially flat remainder of the body to define an upwardly facing concave chin support extending transversely from the upper central portion of the front section, the chin support being unitary with a portion of the central portion of the front section;

a first fastener strip attached to the body;

a second fastener strip for matingly engaging with the first strip, extending from the body sufficiently to overlap the first fastener when the body is formed into the tubular shape; and at least one strip comprising a flexible foam material mounted on one side of the body and forming an inner side of the tubular shape when the body is into the tubular shape.

11. A cervical collar including a normally flat bendable front collar portion and a normally flat, bendable rear collar portion, the front collar portion including a frontal body section fabricated from a plastic material and at least one strip of a compressible, flexible foam material mounted to one side of the frontal body section, the collar further including a first fastener strip attached to one of the front collar portion and the rear collar portion and a second fastener strip, matingly engageable with the first strip, extended from a free edge with a remaining one of the front and rear collar portions so as to engage with the first fastener strip when the front collar portion and rear collar portion are bent together into a tubular shape, wherein the frontal body section is premolded so as to project outwardly on a side of the front collar portion opposite the one side with the foam strip from between substantially co-planar edge portions of the front collar portion and to define at least a unitary chin support extending transversely in the upper central portion of the front collar portion.

12. The cervical collar of claim 11 further comprising a mandible support extending from the chin support to a point proximal a free edge of the front collar portion, wherein the mandible support is sufficiently flexible to conform to the patient wearing the collar.

13. The cervical collar of claim 12 wherein the mandible support is unitary with the front collar portion.

14. The cervical collar of claim 12 wherein the mandible support is a separate molded section attached to the front collar portion.

15. The cervical collar of claim 12 wherein the mandible support is unitary with the front collar portion.

16. The cervical collar of claim 12 wherein the mandible support is a separate molded section attached to the front collar portion.

17. The cervical collar of claim 2 wherein the mandible support is unitary with the front collar portion.

18. The cervical collar of claim 2 wherein the mandible support is a separate molded section attached to the front collar portion.

19. The cervical collar of claim 1 wherein the front collar portion and rear collar portion comprise a bendable unitary body.

20. The collar of claim 11 wherein the frontal body section further includes a pair of elongated openings flanking opposing sides of the unitary chin support to define a pair of lateral upper edge portions integral with the upper central portion, each lateral upper edge portion coupled with a remainder of the body at an end of a proximal one of the pair of elongated openings remote from the transversely extending upper central portion through a hinge.

21. A cervical collar comprising:

a main body portion fabricated from a substantially incompressible plastic material, the main body portion comprising a front body section having a first substantially flat shape and being bendable into a second substantially tubular shape, said front body section having a central portion, an opposed laterally extending right side portion and an opposed laterally extending left side portion, and a mandible support member fabricated from a substantially incompressible plastic material comprising a chin support, an upper right side lateral portion and an upper left side lateral portion, said chin support being unitarily formed with the central portion of said front body section, said upper right side lateral portion and said upper left side lateral portion extending respectively from either side of said chin support, said upper right side lateral portion having a distal end connected at said laterally extending right side portion of said front body section and said upper left side lateral portion having a distal end being connected at said laterally extending left side portion of said front body section.

22. The cervical collar of claim 21 further comprising a separate rear body section, at least one first fastening means attached to said rear body portion, and at least one second fastening means attached to the frontal body section, said at least one second fastening means engaging said at least one first fastening means when the collar is placed around the neck of a user.

23. The cervical collar of claim 21 wherein said upper right side lateral portion and said upper left side lateral portion are capable of moving independently of each other and of the main body portion.

24. The cervical collar of claim 21 wherein said upper right side lateral portion has a proximal end connected to said chin support, said upper left side lateral portion having a proximal end connected to said chin support, the proximal end of said upper right side lateral portion and said upper left side lateral portion including notches for facilitating movement of the upper right and upper left side lateral portions.

25. The cervical collar of claim 21 further comprising at least one strip of foam material mounted to an inner side of the main body portion.

26. The cervical collar of claim 25 wherein the main body portion further comprises embossed rivets for receiving fasteners for securing said at least one strip of foam material.

27. The cervical collar of claim 21 wherein said upper right side lateral portion is unitarily connected by a portion by a portion having a reduced cross-section to said laterally extending right side portion and said upper left side lateral portion is unitarily connected by a portion having a reduced cross-section to said laterally extending left side portion.

28. The cervical collar of claim 27 wherein said reduced cross-section portions comprise a groove living hinge.

29. A cervical collar comprising:
   a main body portion fabricated from a substantially incompressible plastic material, the main body portion comprising a front body section having a first substantially flat shape and being bendable into a second substantially tubular shape, said front body section having a central portion, a laterally extending right side portion and an opposed laterally extending left side portion; and
   a mandible support having an upwardly facing concave chin support fixedly attached to and transversely extending from the central portion of said front body section,
   a portion of said central portion, a portion of said right side portion, a portion of said left side portion, and said chin support being a unitary preformed molding.

30. The cervical collar of claim 29 wherein said mandible support further includes an upper right side lateral portion and an upper left side lateral portion, said upper right side lateral portion and said upper left side lateral portion extending respectively from either side of said chin support, said upper right side lateral portion having a distal end connected at said laterally extending right side portion of said front body section and said upper left side lateral portion having a distal end being connected at said laterally extending left side portion of said front body section; said upper right side lateral portion and said upper left side lateral portion also form part of said unitary preformed molding.

31. A cervical collar comprising:
   a main body portion fabricated from a substantially incompressible plastic material, the main body portion comprising a front body section having a first substantially flat shape and being bendable into a second substantially tubular shape, said front body section having a central portion, a laterally extending right side portion and an opposed laterally extending left side portion; and
   a means for supporting the chin of a wearer, said chin support means having an upwardly facing concave shape, being fabricated from a substantially incompressible plastic material, and being unitary with a portion of the central portion of said front body section.

32. The cervical collar of claim 31 further comprising a means for supporting the right side mandible of a wearer and a means for supporting the left side mandible of a user, said right side mandible support means and said left side mandible support means extending respectively from either side of said chin support means, said right side mandible support means having a distal end connected at said laterally extending right side portion of said front body section, and said left side mandible support means having a distal end being connected at said laterally extending left side portion of said front body section.

33. The cervical collar of claim 21 wherein at least a portion of said central portion, said chin support, and at least a portion of said upper right side lateral portion and said upper left side lateral portion are of varying thickness.

34. A cervical collar comprising:
   a main body portion fabricated from a substantially incompressible plastic material, the main body portion comprising a front body section having a first substantially flat shape and being bendable into a second substantially tubular shape;
   the front body section having a central portion, a laterally extending first side portion and an opposed laterally extending second side portion,
   the central portion having a medial central portion and an upper central portion, the upper central portion extending transversely from the medial central portion and being connected to the medial central portion, the medial central portion having an outwardly curved configuration extending in an arc transversely and outwardly beyond the outward extent of the first and second side portions when the main body portion is in the substantially flat shape, the upper central portion defining an upwardly facing concave chin support, the chin support being unitary with the medial central portion.

35. A cervical collar comprising:
   a main body portion fabricated from a substantially incompressible plastic material, the main body portion comprising a front body section having a first substantially flat shape and being bendable into a second substantially tubular shape;
   the front body section having a central portion, a laterally extending first side portion and an opposed laterally extending second side portion;
   the central portion having a medial central portion and an upper central portion the upper central portion extending transversely from the medial central portion and being connected to the medial central portion, the medial central portion having an outwardly curved configuration extending in an arc transversely and outwardly beyond the outward extent of the first and second side portions when the main body portion is in the substantially flat shape, the upper central portion defining an upwardly facing concave chin support, the chin support being unitary with a portion of the medial central portion, the portion of the medial central portion being connected to the main body portion.

36. A cervical collar comprising:
   a main body portion fabricated from a substantially incompressible plastic material, the main body portion comprising a front body section having a first substantially flat shape and being bendable into a second substantially tubular shape;
   the front body section having a central portion, a laterally extending first side portion and an opposed laterally extending second side portion,
   the central portion having a medial central portion and an upper central portion, the upper central portion extending transversely from the medial central portion and being connected to the medial central portion, the medial central portion having an outwardly curved configuration extending in an arc transversely and outwardly beyond the outward extent of the first and second side portions when the main body portion is in the substantially flat shape, the upper central portion defining an upwardly facing concave chin support, the chin support comprising a transversely extending chin support portion and a downwardly extending mounting portion, the mounting portion being unitary with a portion of the medial central portion.

37. A cervical collar comprising:
   a main body portion fabricated from a substantially incompressible plastic material, the main body portion comprising a front body section having a first substantially flat shape and being bendable into a second substantially tubular shape;

the front body section having a central portion, a laterally extending first side portion and an opposed laterally extending second side portion;

the central portion having a medial central portion and an upper central portion, the upper central portion extending transversely from the medial central portion and being unitary with the medial central portion, the medial central portion having an outwardly curved configuration extending in an arc transversely and outwardly beyond the outward extent of the first and second side portions when the main body portion is in the substantially flat shape, the upper central portion defining an upwardly facing concave chin support.

38. A cervical collar comprising:

a main body portion fabricated from a substantially incompressible plastic material comprising a front body section having a central portion, a laterally extending first side portion and an opposed laterally extending second side portion; and a chin support fabricated from a substantially incompressible plastic material and having a substantially T-shape, the chin support having an upper chin support member extending transversely from the main body portion and a downwardly extending member unitary with the upper chin support member, the downwardly extending member being attached to the central portion of the front body section.

39. The cervical collar of claim 38 wherein the downwardly extending member is unitary with the central portion.

40. The cervical collar of claim 38 wherein the chin support further comprises an upper first side portion extending from the chin support and having a distal end connected to the first side portion; and a laterally extending upper second side portion extending from the chin support and having a distal end connected to the second side portion.

41. The cervical collar of claim 40 wherein the downwardly extending member is unitary with the central portion.

42. The cervical collar of claim 38 wherein the main body further comprises a rear body section and the front body section further comprises a foam strip attached to an inner side of the front body section.

43. A cervical collar comprising:

a main body portion fabricated from a substantially incompressible plastic material and comprising a front body section having a first substantially flat shape and being bendable into a second substantially tubular shape, the front body section having a central portion, a laterally extending first side portion and an opposed laterally extending second side portion; and a mandible support fabricated from a substantially incompressible plastic material comprising a transversely extending chin support located at the center of the central portion, an upper first side portion, an upper second side portion, the upper first side portion and the upper second side portion extending respectively from either side of the chin support, the upper first side portion having a distal end attached to a distal end of the first side portion, the upper second side portion having a distal end attached to a distal end of the second side portion, and the chin support being unitarily connected to a portion of the central portion.

44. A cervical collar comprising:

a main body portion fabricated from a substantially incompressible plastic material and comprising a front body section having a first substantially flat shape and being bendable into a second substantially tubular shape, the front body section having a central portion, a laterally extending first side portion and an opposed laterally extending second side portion; and a mandible support fabricated from a substantially incompressible plastic material comprising a centrally located chin support, an upper first side portion, an upper second side portion, the upper first side portion and the upper second side portion extending respectively from either side of the chin support, the upper first side portion having a distal end attached to a distal end of the first side portion, the upper second side portion having a distal end attached to a distal end of the second side portion, and the chin support being unitarily connected to a portion of the central portion, and an opening formed between the upper first side portion and the first side portion and an opening formed between the upper second side portion and the second side portion.

45. The cervical collar of claim 43 wherein the chin support is unitary with a portion of the central portion, the portion of the central portion being connected to the main body portion.

46. The cervical collar of claim 43 wherein the central portion is thicker and less flexible than the first and second side portions.

47. A cervical collar comprising:

a main body portion fabricated from a substantially incompressible plastic material and comprising a front body section having a first substantially flat shape and being bendable into a second substantially tubular shape, the front body section having a central portion, a laterally extending first side portion and an opposed laterally extending second side portion; and a mandible support fabricated from a substantially incompressible plastic material comprising a centrally located chin support, an upper first side portion, an upper second side portion, the chin support comprising a transversely extending chin support portion and a downwardly extending mounting portion, the upper first side portion and the upper second side portion extending respectively from either side of the chin support, the upper first side portion having a distal end attached to a distal end of the first side portion, the upper second side portion having a distal end attached to a distal end of the second side portion, and, the mounting portion being unitarily connected to a portion of the central portion.

48. The cervical collar of claim 47 wherein the mounting portion is unitary with a portion of the central portion.

49. The cervical collar of claim 43 wherein the distal end of the upper first side portion is unitarily connected to the first side portion and the distal end of the upper second side portion is unitarily connected to the second side portion.

50. A cervical collar comprising:

a main body portion fabricated from a substantially incompressible plastic material and comprising a front body section having a first substantially flat shape and being bendable into a second substantially tubular shape, the front body section having a central portion, a laterally extending first side portion and an opposed laterally extending second side portion; and a mandible support fabricated from a substantially incompressible plastic material comprising a centrally located chin support, an upper first side portion, an upper second side portion, the upper first side portion and the upper second side portion extending respectively from either side of the chin support, the upper first side portion having a distal end attached to a distal end of the first side portion, the upper second side portion having a distal end attached to a distal end of the second side portion, and the chin support being unitarily connected to a portion of the central portion, the chin support comprising an outer chin support portion and an inner chin support portion, the outer chin support portion extending transversely beyond an outer extent of the central portion and the inner chin support portion extending transversely within the outward extent of the central portion.

51. The cervical collar of claim 50 wherein the outer chin support portion extends slightly upwardly and the inner chin support portion extends slightly downwardly.

* * * * *